US00PP12850P2

(12) United States Plant Patent
Griesbach et al.

(10) Patent No.: US PP12,850 P2
(45) Date of Patent: Aug. 13, 2002

(54) ORNITHOGALUM PLANT NAMED 'CHESAPEAKE STARLIGHT'

(75) Inventors: Robert Griesbach, Ellicott City, MD (US); Fred Meyer, *deceased*, late of Escondido, CA (US), by Marlene Estella Meyer, administrator

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 43 days.

(21) Appl. No.: 09/765,319

(22) Filed: Jan. 22, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A new and distinct cultivar of Ornithogalum plant named 'Chesapeake Starlight' characterized by its strong, upright and long scapes; and dense corymbose racemes with numerous white-colored flowers.

1 Drawing Sheet

BACKGROUND OF THE INVENTION

The present Invention relates to a new and distinct cultivar of Ornithogalum plant, botanically known as *Ornithogalum thyrsoides*, and hereinafter referred to by the name 'Chesapeake Starlight'.

The new Ornithogalum is a product of a planned breeding program conducted by the Inventors in Beltsville, Md. and Escondido, Calif. The objective of the breeding program was to create new freely-flowering Ornithogalums with unique and desirable flower colors and strong and tall scapes.

The new Ornithogalum originated from a self-pollination of a selection originating from a cross made by the Inventors of the *Ornithogalum thyrsoides* cultivar Bok Bay, not patented, with an unidentified selection of *Ornithogalum thyrsoides*, not patented. The cultivar Chesapeake Starlight was discovered and selected by the Inventors as a flowering plant within the progeny of the stated cross in a controlled environment in Beltsville, Md. in 1994.

Asexual reproduction of the new Ornithogalum by tissue culture in a controlled environment in a laboratory in Beltsville, Md., has shown that the unique features of this new Ornithogalum are stable and reproduced true to type in successive generations.

SUMMARY OF THE INVENTION

The cultivar 'Chesapeake Starlight' has not been observed under all possible environmental conditions. The phenotype may vary somewhat with variations in environment such as temperature, daylength, light intensity, and water or nutritional status without, however, any variance in genotype.

The following traits have been repeatedly observed and are determined to be the unique characteristics of 'Chesapeake Starlight'. These characteristics in combination distinguish 'Chesapeake Starlight' as a new and distinct Ornithogalum:

1. Strong, upright and long scapes.

2. Dense corymbose racemes with numerous white-colored flowers.

In side-by-side comparisons conducted by the Inventors in Beltsville, Md., plants of the new Ornithogalum differ from plants of the cultivar Bok Bay, in the following characteristics:

1. Plants of the new Ornithogalum flower about five weeks earlier than plants of the cultivar Bok Bay.

2. Plants of the new Ornithogalum have longer scapes than plants of the cultivar Bok Bay.

3. Plants of the new Ornithogalum have white-colored flowers whereas plants of the cultivar Bok Bay have cream-colored flowers.

In side-by-side comparisons conducted by the Inventors in Beltsville, Md., plants of the new Ornithogalum differ from plants of unidentified selection of *Ornithogalum thyrsoides*, in the following characteristics:

1. Plants of the new Ornithogalum are more freely flowering than plants of the unidentified selection of *Ornithogalum thyrsoides.*

2. Plants of the new Ornithogalum have stronger scapes than plants of the unidentified selection of *Ornithogalum thyrsoides.*

3. Plants of the new Ornithogalum have a denser (less open) flower display than plants of the unidentified selection of *Ornithogalum thyrsoides.*

BRIEF DESCRIPTION OF THE PHOTOGRAPH

The accompanying colored photograph illustrates the overall appearance of the new Ornithogalum, showing the colors as true as it is reasonably possible to obtain in colored reproductions of this type. Colors in the photograph may differ slightly from the color values cited in the detailed botanical description which accurately describe the colors of the new Ornithogalum. The photograph comprises a close-up view of a typical inflorescence of 'Chesapeake Starlight'.

DETAILED BOTANICAL DESCRIPTION

In the following description, color references are made to The Royal Horticultural Society Colour Chart except where general terms of ordinary dictionary significance are used. The following observations and measurements describe plants grown in Beltsville, Md., under commercial practice in a glass-covered greenhouse. During the production of the plants, day temperatures ranged from 18 to 27° C. and night temperatures ranged from 13 to 21° C. Measurements and numerical values represent averages for typical flowering plants. Plants used for the description and photograph were grown in 12.5-cm containers for about 20 to 25 weeks after planting rooted tissue-cultured plantlets in the fall.

Botanical classification: *Ornithogalum thyrsoides* cultivar Chesapeake Starlight.

Parentage: Self-pollination of a selection originating from a cross of an unidentified selection of *Ornithogalum thyrsoides*, not patented, with the *Ornithogalum thyrsoides* cultivar Bok Bay, not patented.

Propagation:

*Type.*—Tissue culture.

*Time to initiate roots from tissue-cultured micro-cuttings.*—About 10 days at 24° C.

*Root description.*—Quantity: About 30 to 40 primary roots arising from bulb. Diameter: About 12 to 13 cm. Color: 159C.

*Bulb description.*—Appearance: Tunicate. Diameter: About 3.5 cm. Circumference: About 11 to 11.5 cm. Color: 161B.

Plant description:

*Plant form.*—Upright flowering potted plant; inverted triangle. Leaves basal with central flowering stem. Flowers arranged in dense corymbose racemes.

*Crop time.*—Usually about 20 to 25 weeks are required to produce finished flowering plants in 12.5-cm containers from rooted tissue-culture plantlets.

*Plant height.*—About 55 to 60 cm.

*Plant width.*—About 30 to 40 cm.

*Leaves.*—Arrangement: Simple; basal; rosette; sessile. Quantity of leaves per plant: About 6 to 8. Length: About 25 to 30 cm. Width: About 3.5 to 4 cm. Shape: Lanceolate. Apex: Acute. Margin: Entire. Texture: Upper and lower surfaces: glabrous, smooth; longitudinally ridged. Color: Young and mature leaves, upper and lower surfaces: 143B; upper surface, slightly glossy; venation, 143B. Leaf sheath: Length: About 3.5 to 4 cm. Width: About 5.5 to 6 cm. Color: 155B.

Flower description:

*Flowering habit.*—Inflorescences scapose with single flowers, 3-merous, arranged in dense corymbose racemes. Flowers not fragrant; flowers persistent.

*Natural flowering season.*—Plants flower during the spring; flowering recurrent.

*Flower longevity on the plant.*—Individual flowers last about one week; inflorescence last about six weeks.

*Flower longevity as a cut flower.*—Inflorescences last about 5 to 6 weeks.

*Inflorescence size.*—Length: About 60 cm. Width: About 8 cm.

*Flower buds.*—Length: About 1.2 to 1.5 cm. Diameter: About 8 to 10 mm. Shape: Ovoid. Color: 145B.

*Flowers.*—Quantity of flowers and flower buds per plant: About 50 to 60 per flowering stem; each bulb produces about three flowering stems. Shape: Circular. Diameter: About 3.5 to 4 cm. Depth (height): About 2 cm.

*Perianth.*—Quantity/arrangement: Three petals and three sepals per flower; separate. Length: About 2 to 2.5 cm. Width: About 1.5 cm. Shape: Pyriform. Apex: Slightly acute. Margin: Entire. Texture: Upper and lower surfaces: smooth, waxy. Color: When opening, upper and lower surfaces: 155A. Fully opened, upper and lower surfaces: Apex and center, 155D; base, 152A; glossy.

*Scape.*—Angle: Erect. Strength: Strong. Length: About 50 cm. Diameter: About 1 cm. Texture: Glabrous. Color: 137A.

*Pedicels.*—Strength: Strong. Length: About 4.5 to 5 cm. Diameter: About 3 mm. Texture: Glabrous. Color: 144B.

*Flower bracts.*—Arrangement: Single, subtending the perianth. Length: About 4 to 4.5 cm. Width: About 1.2 to 1.5 cm. Shape: Cymbiformis. Color: 137A.

*Reproductive organs.*—Stamens: Quantity: Six. Anther shape: Oval. Anther length: About 2 to 3 mm. Anther color: 163B. Amount of pollen: Moderate. Pollen color: 163B. Pistils: Quantity: One. Length: About 8 to 10 mm. Stigma shape: Tri-sulcate. Stigma color: 158A. Style length: About 2 mm. Style color: 158A. Ovary color: 146B.

*Seed.*—Seed production has not been observed.

Disease resistance: Resistance to pathogens common to Ornithogalums has not been determined.

It is claimed:

1. A new and distinct cultivar of Ornithogalum plant named 'Chesapeake Starlight', as illustrated and described.

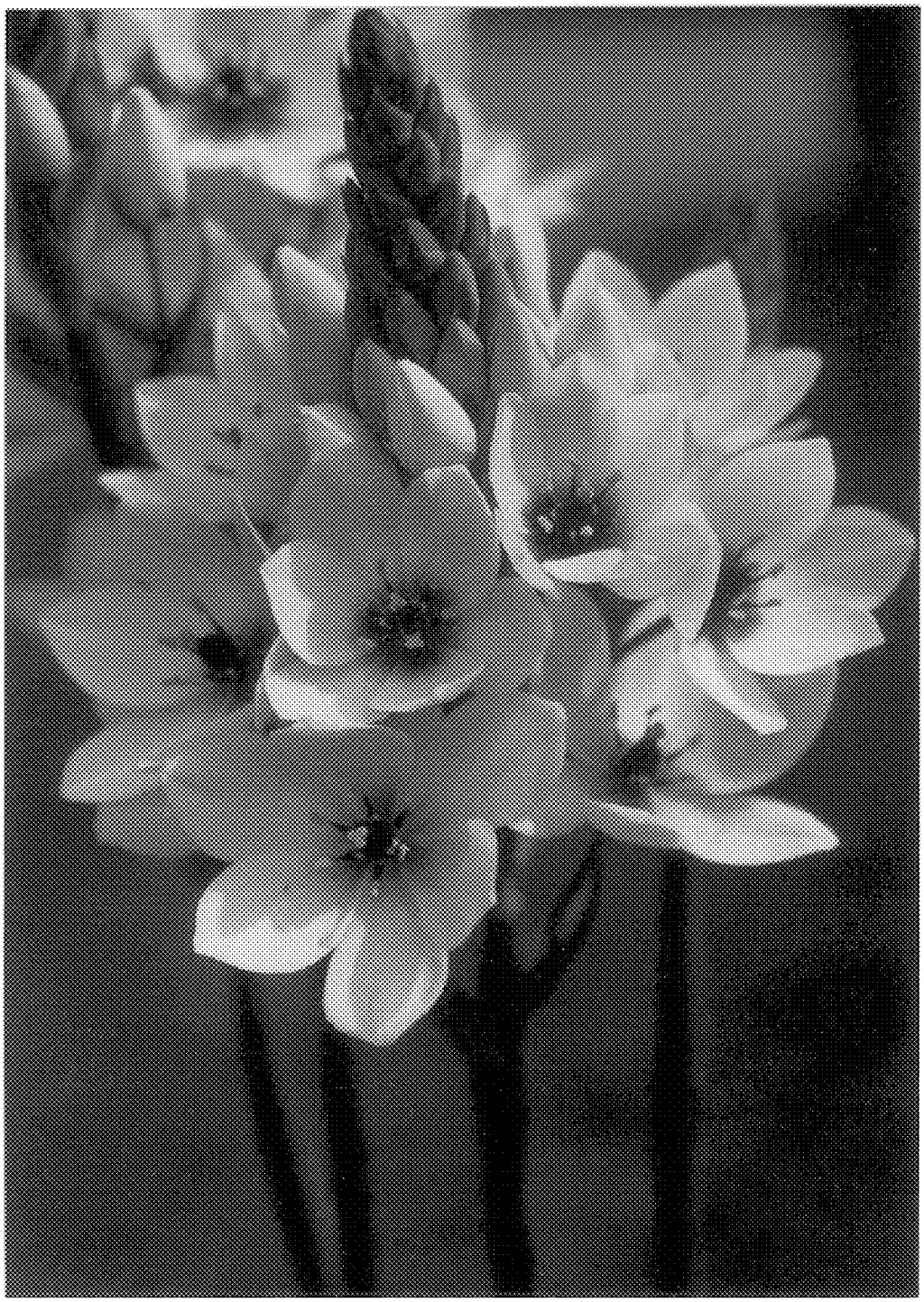

* * * * *